United States Patent [19]

Asakura et al.

[11] Patent Number: 4,999,295

[45] Date of Patent: Mar. 12, 1991

[54] BIOCATALYST ENTRAPPED IN A SILK FIBROIN MEMBRANE

[75] Inventors: Tetsuro Asakura; Makoto Demura, both of Koganei; Takeshi Kuroo, Tokyo, all of Japan

[73] Assignee: Terumo Kabushiki Kaisha, Tokyo, Japan

[21] Appl. No.: 176,687

[22] Filed: Apr. 1, 1988

[30] Foreign Application Priority Data

May 8, 1987 [JP] Japan .................................. 62-110681
Oct. 2, 1987 [JP] Japan .................................. 62-248215
Mar. 11, 1988 [JP] Japan .................................. 63-57941

[51] Int. Cl.$^5$ ..................... C12N 11/02; C12N 11/04; C12Q 1/00; G01N 27/26
[52] U.S. Cl. .................................. 435/177; 204/403; 435/182; 435/817
[58] Field of Search ............... 435/174, 177, 182, 817; 204/403

[56] References Cited

PUBLICATIONS

Demura et al., "Structural Characteristics of Silk and Application to Enzyme-Fixed Materials," report published in the 57th Lecture Meeting of the Japanese Society of Sericultural Science at Yatabe-cho, Ibaraki-ken, Japan on Apr. 3, 1987.
Demura et al., "Fine Structure of Silk Fibroin Membrane and Activity of Immobilized Enzyme," report published in the 36th Convention of the Society of Polymer Science, Japan at Kokuritsu Kyoto Kokusai Kaikan on May 29, 1987.
Kobos, R. K., Trends in Analytical Chemistry, vol. 2, No. 7, 1983, pp. 154–157.
Kuzuhara et al., Journal of Biotechnology, vol. 5, 1987, pp. 199–207.

*Primary Examiner*—David M. Naff
*Attorney, Agent, or Firm*—Burns, Doane, Swecker & Mathis

[57] ABSTRACT

A silk fibroin membrane containing an entrapped biocatalyst such as an enzyme or microorganism is provided by forming a mixture of a biocatalyst solution and a silk fibroin solution, forming a membrane by casting the mixture, drying the membrane and mechanically treating the resultant membrane at a temperature and humidity to produce the membrane in $\beta$-form and to structurally stabilize the membrane. Mechanically treating may be by stretching or compressing. A biocatalyst sensor is formed by coating an electrically conductive substrate with a gas-permeable layer and coating the gas-permeable layer with the silk fibroin membrane containing an entrapped biocatalyst.

12 Claims, 15 Drawing Sheets

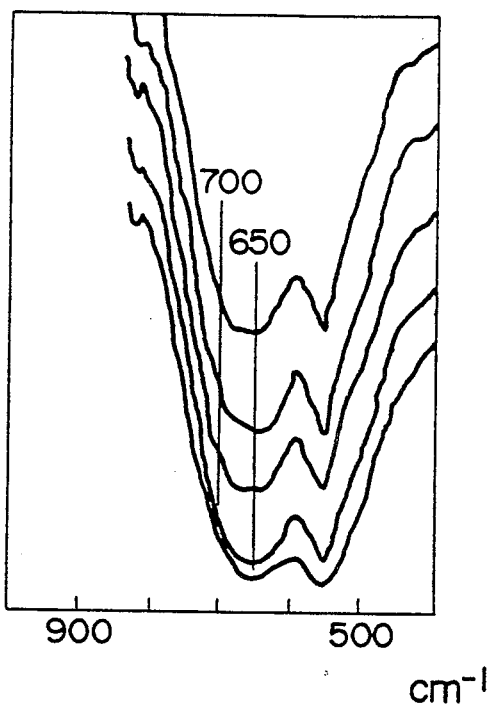
F I G. 1
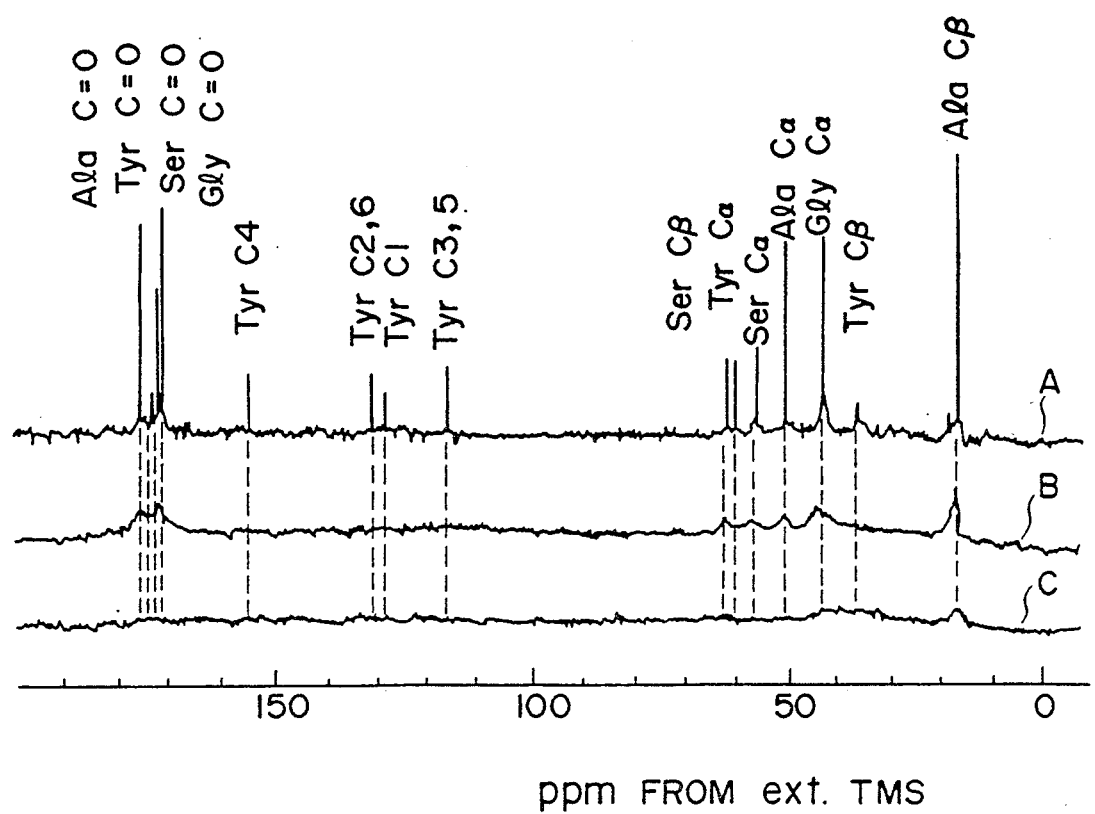
F I G. 2

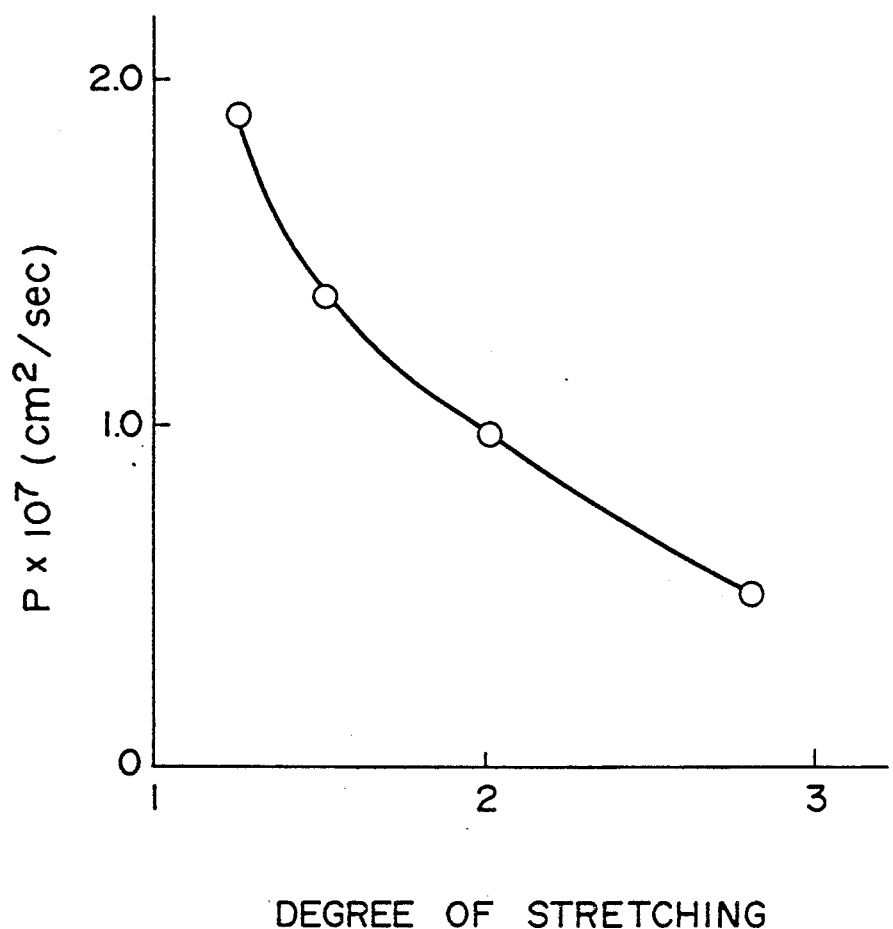
F I G. 3

|  | Km (mV) | Vm (U/mg) | Vm (U/mg/cm$^2$) |
|---|---|---|---|
| GOD | 25.2 | 103.3 | — |
| DR 1.25 | 4.0 | 7.6 | 3.1 |
| DR 3.0 | 5.4 | 9.8 | 2.0 |
| ME 30 | 4.5 | 4.9 | 2.5 |
| ME 3 | 3.8 | 4.4 | 2.2 |
| ME 24 | 4.9 | 4.3 | 2.2 |

TEMPERTURE 25°C, pH = 7.0

F I G. 5

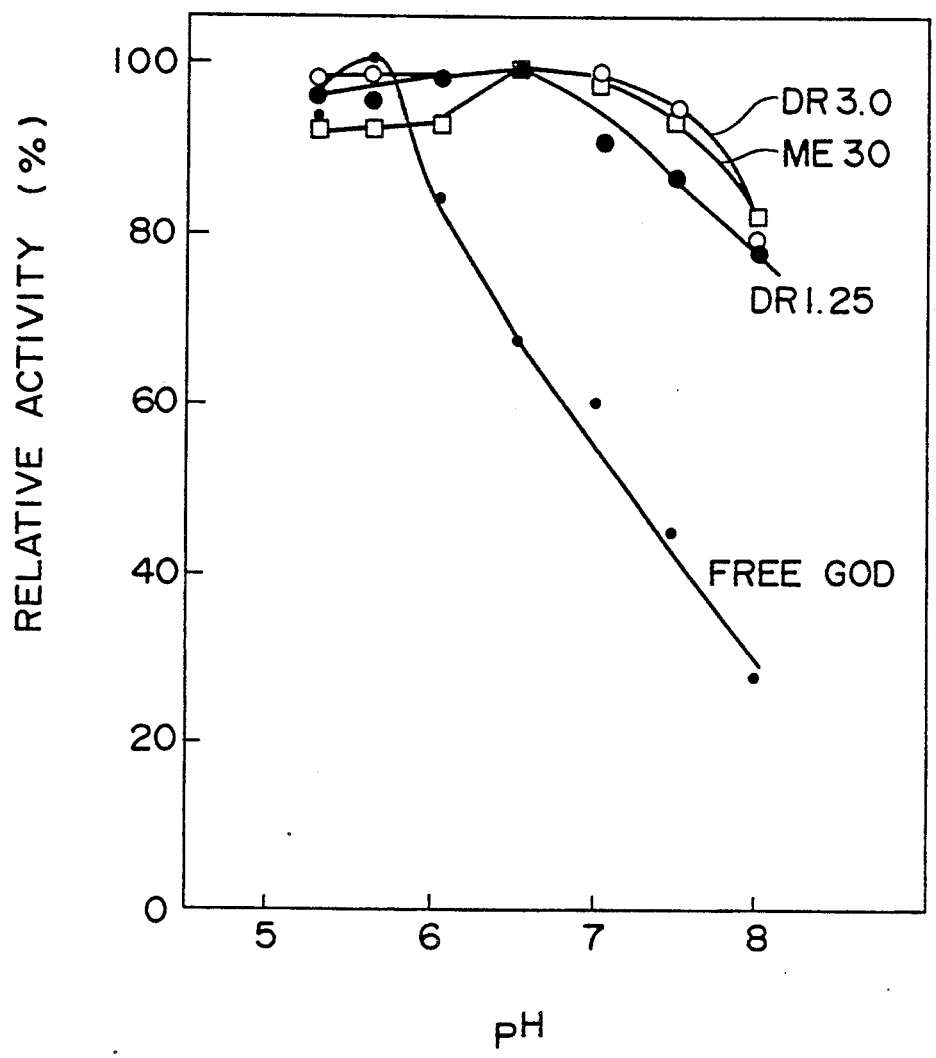
F I G. 6

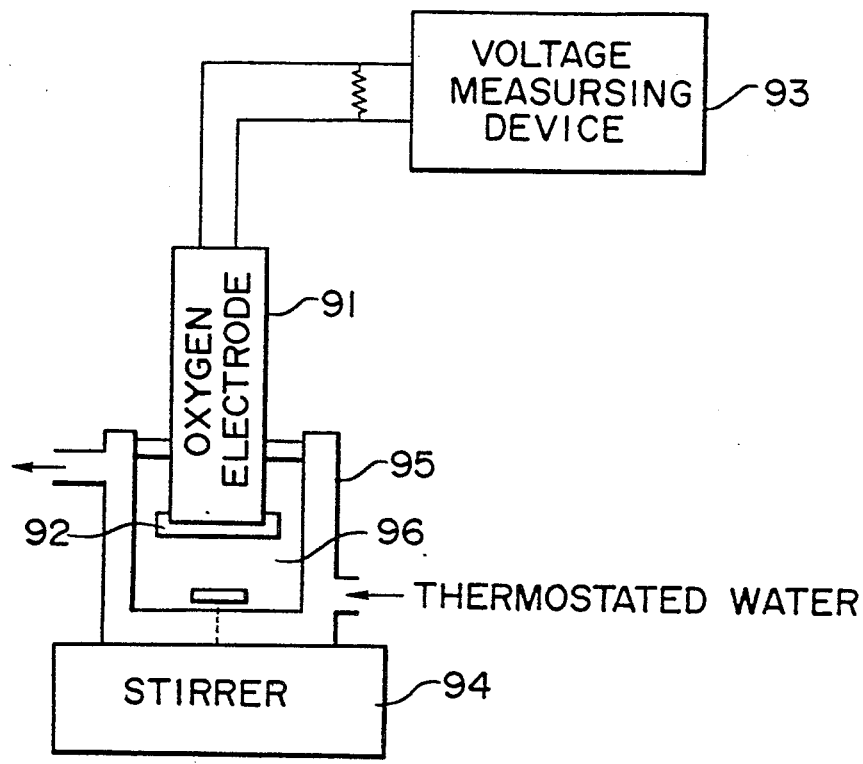
F I G. 9 (a)
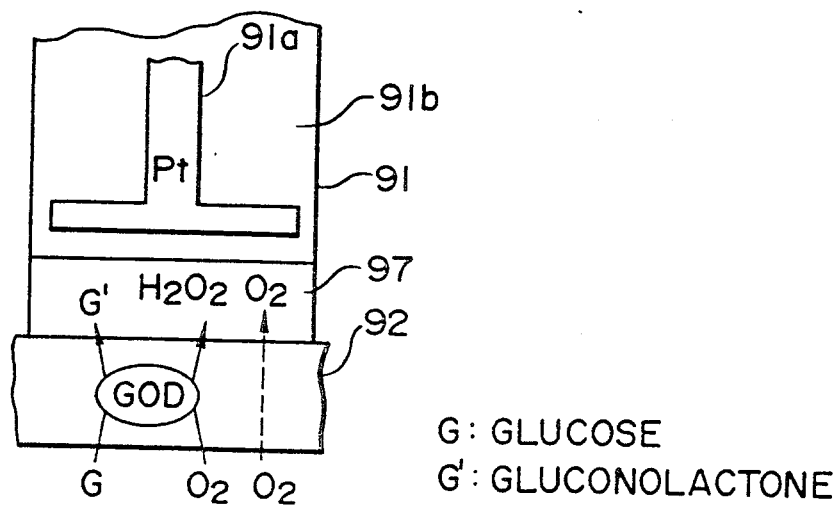
G: GLUCOSE
G': GLUCONOLACTONE
F I G. 9 (b)

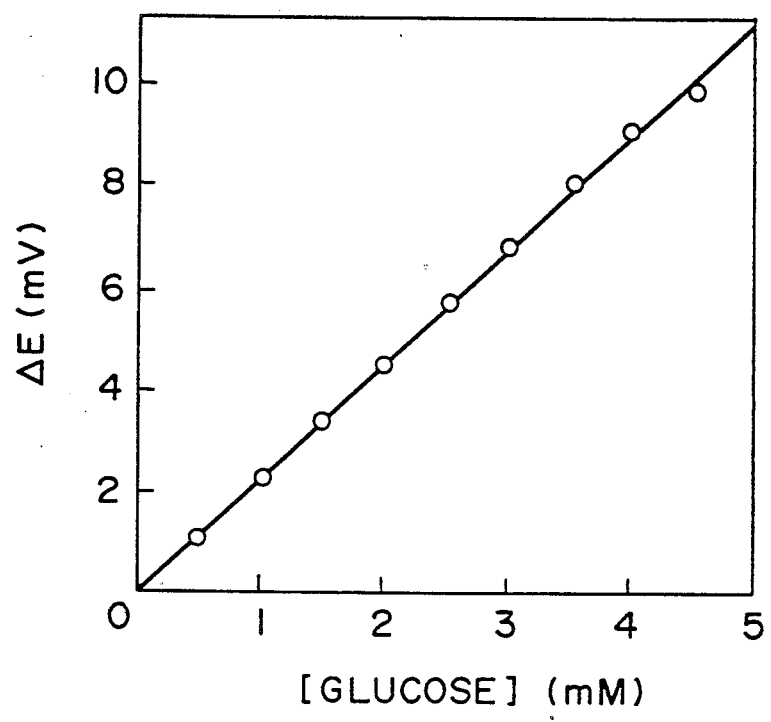
F I G. 10

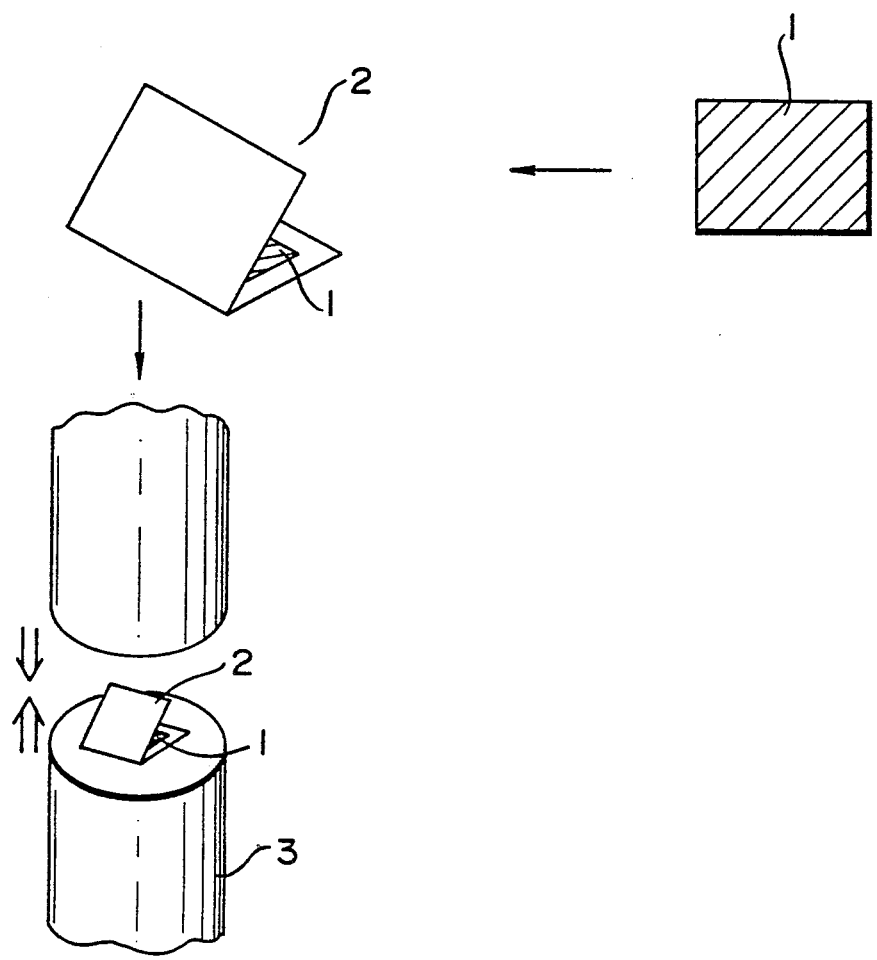
F I G. 11

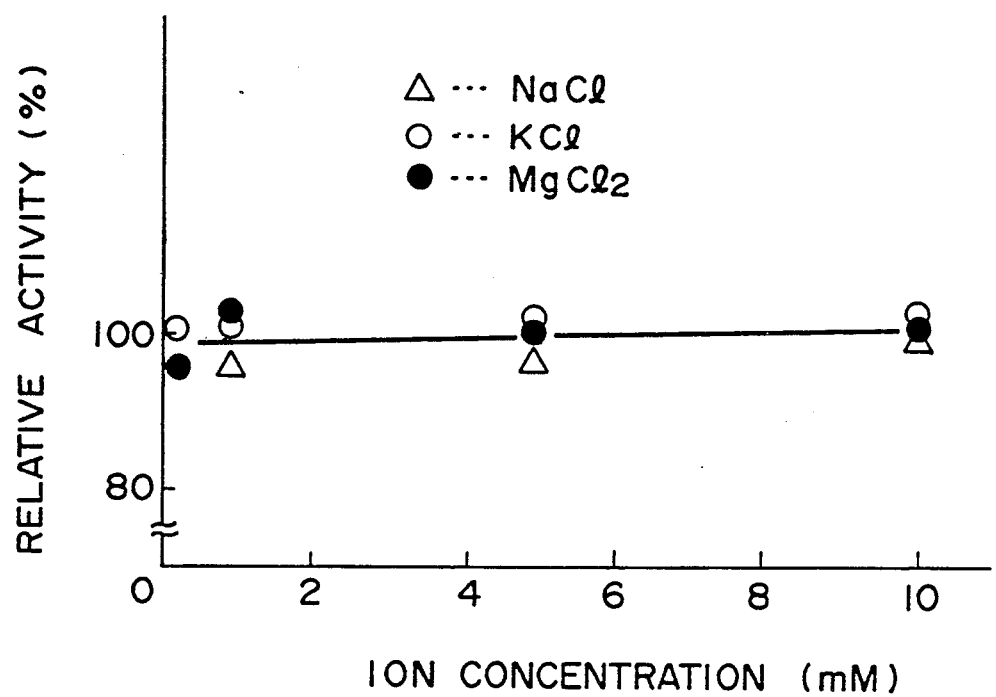
F I G. 13

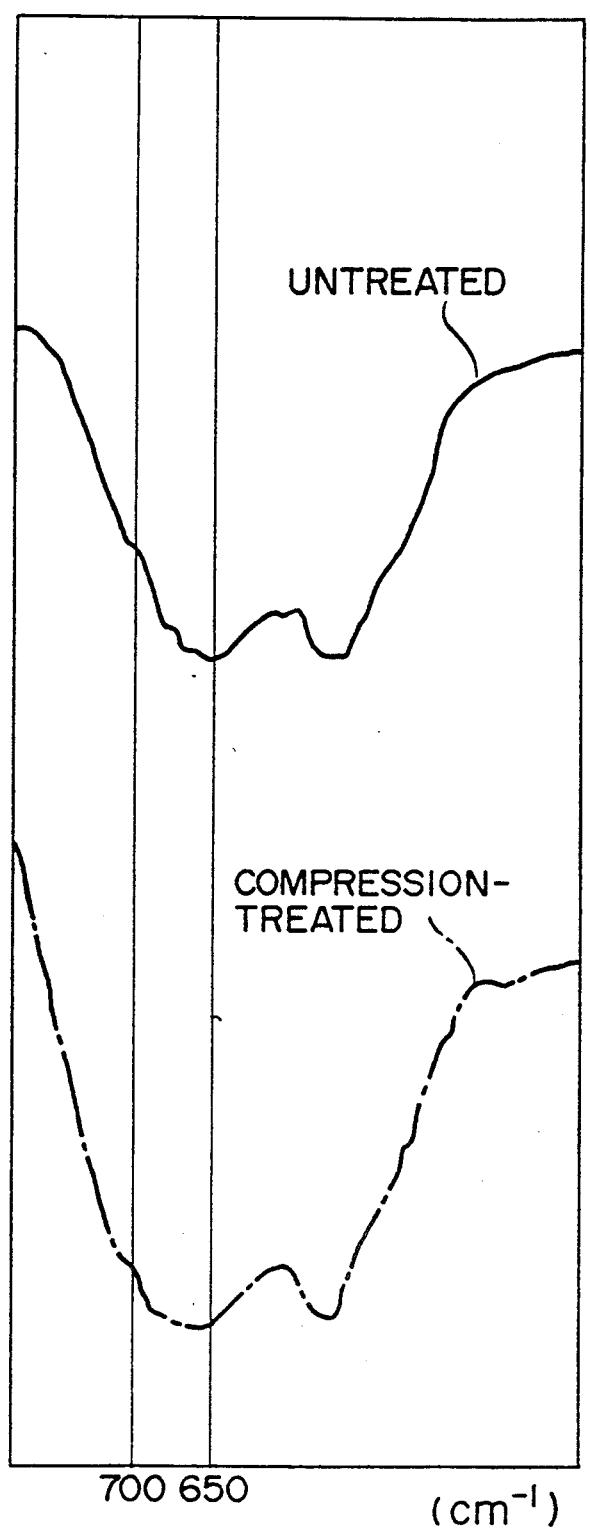
F I G. 15

BIOCATALYST ENTRAPPED IN A SILK FIBROIN MEMBRANE

BACKGROUND OF THE INVENTION

1. Field of the Invention

This invention relates to a biocatalyst-fixed membrane, a method of manufacturing the biocatalyst-fixed membrane, and a biocatalyst sensor using the biocatalyst-fixed membrane. More particularly, the invention relates to a biocatalyst-fixed membrane such as an enzyme or microorganism fixed membrane which effectively exploits the manufacturing characteristics of silk fibroin, the manufacture of the membrane and a biocatalyst sensor using the same.

2. Description of the Prior Art

When a biocatalyst is fixed by an entrapping method in the prior art, the fixed carrier often requires a cross-linking treatment with glutaric aldehyde or the other compounds in order to achieve insolubilization. However, the secondary deactivation of biocatalyst due to heat, strong acids and alkalis, organic solvents and so on cannot be avoided, and the activity in the membrane almost completely vanishes within only one month.

SUMMARY OF THE INVENTION

An object of the present invention is to provide a biocatalyst-fixed membrane, a method of manufacturing the same and an biocatalyst sensor using the membrane, in which, by exploiting the structural characteristics of silk fibroin to employ the same as a biocatalyst entrapped fixed material, the stability of the biocatalyst-containing membrane against heat or pH change is raised, the leakage of biocatalyst is minimized and biocatalyst stability is prolonged.

In accordance with the present invention, there is provided an biocatalyst-fixed membrane in which a biocatalyst-fixed silk fibroin membrane is structurally stabilized by a stretching treatment.

In accordance with the present invention, there is also provided a method of manufacturing a biocatalyst-fixed membrane comprising the steps of mixing a given amount of a biocatalyst with a silk fibroin solution, forming a biocatalyst-fixed silk fibroin membrane by casting on a substrate with the mixed solution followed by drying, and stretching the biocatalyst-fixed silk fibroin membrane in an atmosphere held at a given temperature and humidity, to structurally stabilize the biocatalyst-fixed fibroin membrane at a given degree of stretching.

According to the invention, there is provided a biocatalyst sensor comprising an electrically conductive substrate, a gas-permeable layer coating the electrically conductive substrate and permeable to a given gas, and a biocatalyst-fixed membrane coating the gas-permeable layer and consisting of a biocatalyst-fixed silk fibroin membrane structurally stabilized by a stretching treatment.

Thus, in accordance with the invention, there are provided a biocatalyst-fixed membrane, a method of manufacturing the same and an biocatalyst sensor using the membrane, in which, by exploiting the structural characteristics of silk fibroin to form the same into a biocatalyst entrapped fixed material, the stability of the biocatalyst-containing membrane is raised, the leakage of biocatalyst is made minimized and biocatalyst stability is prolonged.

In the biocatalyst-fixed membrane and biocatalyst sensor of the invention, the structural change of the biocatalyst-containing *Bombyx mori* regenerated silk fibroin membrane is manifested only by a stretching treatment without any chemical processing. As a result, the following advantages are obtained:

(1) The biocatalyst-containing membrane has a high stability yield.

(2) High stability is obtained when pH and temperature are changed.

(3) The stability of the biocatalyst in the membrane does not change for more than four months.

Another object of the invention is to provide a biocatalyst-fixed membrane, a method of manufacturing the same and a biocatalyst sensor using the membrane, in which, by causing the structural change of a biocatalyst-fixed silk fibroin membrane to be manifested only by a physical treatment to fix a biocatalyst whose activity declines appreciably when it is subjected to a chemical treatment, the stability of a biocatalyst-containing membrane is raised, and the biocatalyst stability is prolonged.

To this end, in accordance with another aspect of the invention, there is provided a method of manufacturing a biocatalyst-fixed membrane comprising the steps of: (a) mixing a given amount of an biocatalyst solution with a silk fibroin solution; (b) forming a biocatalyst-fixed silk fibroin membrane by casting on a substrate with the mixed solution followed by drying; and (c) subjecting said silk fibroin membrane, after being held in an atmosphere at a given temperature and humidity, to a given pressure so as to form at least a part of said silk fibroin membrane into a β-form.

In addition, a fixed membrane in accordance with the present invention is a biocatalyst-fixed membrane constituted by a fixed silk fibroin obtained by mixing a given amount of a biocatalyst solution with a silk fibroin solution and then by casting on a substrate with the mixed solution followed by drying, and at least a part of said biocatalyst-fixed membrane is formed into a β-form by a compression treatment. Furthermore, a biocatalyst sensor in accordance with the present invention comprises: an electrically conductive substrate; a gas-permeable layer coating said electrically conductive substrate and permeable to a given gas; and a biocatalyst-fixed membrane coating said gas-permeable layer and consisting of a biocatalyst-fixed silk fibroin membrane at least a part of which is formed into a β-form by a compression treatment.

In accordance with the present invention, it is possible to provide a biocatalyst-fixed membrane, a method of manufacturing the same and a biocatalyst sensor using the membrane, in which, by exploiting the structural characteristics of silk fibroin to employ the same as an biocatalyst inclusive fixed material, the stability of the biocatalyst-fixed membrane is raised, and the biocatalyst stability is prolonged.

More specifically, since the biocatalyst-fixed membrane of the present invention is arranged such that the structural change of the biocatalyst-containing *Bombyx mori* regenerated silk fibroin membrane is manifested solely by compression without any chemical processing, the following advantages are obtained:

(1) The biocatalyst-containing membrane has a high level of stability.

(2) The stability of the biocatalyst in the membrane remains stable for two months or more without undergoing deactivation.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 shows the infrared spectra of glucose oxidase(GOD)-fixed *Bombyx mori* regenerated silk fibroin membranes;

FIG. 2 shows $^{13}C$ nuclear magnetic resonance spectra of a glucose oxidase-fixed *Bombyx mori* regenerated silk fibroin membranes;

FIG. 3 shows the plot of the glucose permeability of a glucose oxidase-fixed *Bombyx mori* regenerated silk fibroin membrane of Example 1 vs the degree of stretching;

FIG. 5 is a table showing the Michaelis constants Km and maximum reaction rates Vm of glucose oxidase-fixed *Bombyx mori* regenerated silk fibroin membranes of Example 1;

FIG. 6 shows the stability of biocatalyst stability of a glucose oxidase-fixed *Bombyx mori* regenerated silk fibroin membrane of Example 1 with respect to a change in pH;

FIGS. 7 and 10 are graphs illustrating the outputs of a glucose sensor plotted against the glucose concentration of a glucose oxidase-fixed *Bombyx mori* regenerated silk fibroin membrane of Example 1;

FIGS. 9(a), (b) are schematic apparatus of a glucose sensor assembled by coating an oxygen electrode with a glucose oxidase-fixed *Bombyx mori* regenerated silk fibroin membrane embodying the present invention.

FIG. 11 is a schematic diagram illustrating a method of compression treatment of a glucose oxidase-fixed *Bombyx mori* regenerated silk fibroin membrane in accordance with Example 2;

FIG. 13 is a graph illustrating the effect of the presence of ions on the stability of glucose oxidase-fixed *Bombyx mori* regenerated silk fibroin membranes of Example 2;

FIG. 15 is an infrared spectrum diagram of glucose oxidase-fixed *Bombyx mori* regenerated silk fibroin membranes of Example 2.

DESCRIPTION OF THE PREFERRED EMBODIMENT

Figure 4A:
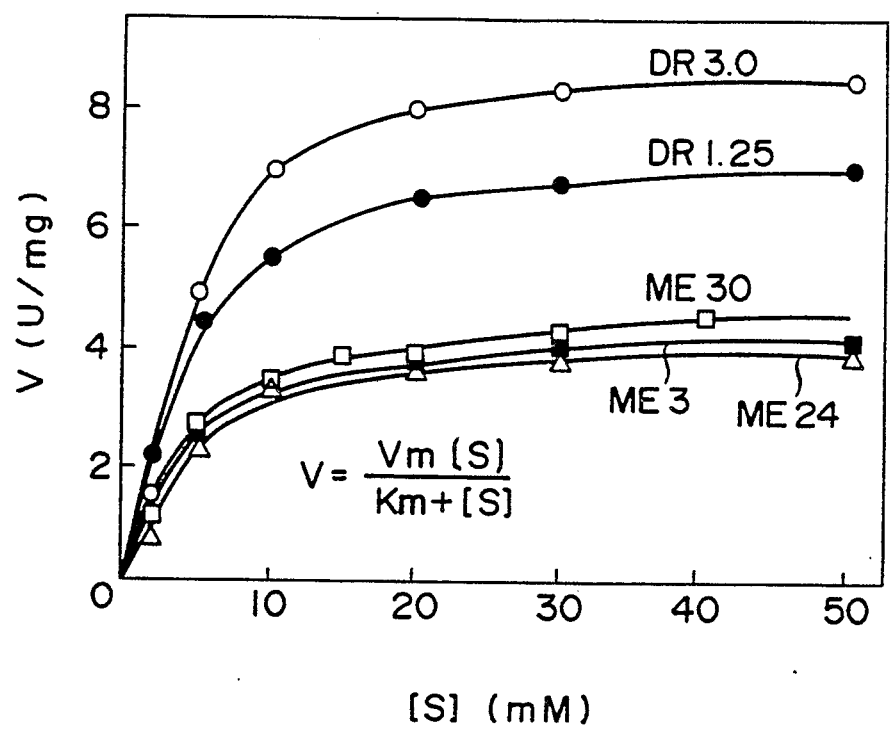
FIGS. 4(a), (b) are the results of measuring biocatalyst activities of glucose oxidase-fixed *Bombyx mori* regenerated silk fibroin membranes of Example 1 by a dissolved oxygen electrode.
Figure 4B:
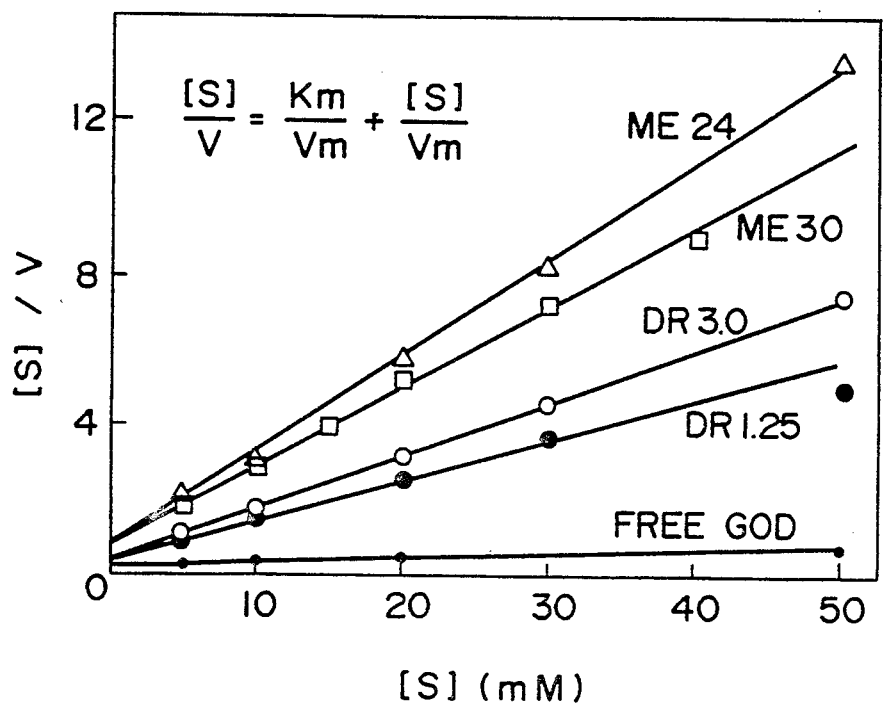

An embodiment of the present invention will now be described in detail with reference to the accompanying drawings.

EXAMPLE 1

Process for Preparing Silk Fibroin Solution

*Bombyx mori* cocoon was degummed with 0.5% Marseilles soap at a cocoon-soap solution ratio of 1:200 for 30 min at a temperature of 100° C. After this was performed twice, the result was washed with distilled water to obtain degummed cocoon.

The degummed cocoon was dissolved at a temperature of 40° C. in a 9 M aqueous solution of lithium bromide (LiBr), and dialyzed after which approximately 4w/w % of a *Bombyx mori* regenerated silk fibroin solution was obtained.

Process for Preparing Biocatalyst-fixed membrane

The solution of *Bombyx mori* regenerated silk fibroin was mixed with 0.2 wt % of the dried fibroin glucose oxidase (GOD). The liquid was cast on an acrylic sheet and dried at 4° C., thereby providing a GOD-fixed regenerated silk fibroin membrane having a membrane thickness of 27 um.

Insolubilization Treatment (1) Example of methanol treatment

The biocatalyst-fixed membranes prepared as described above were subjected to a methanol treatment, which entailed dipping the membranes in an 80% aqueous solution for 30 sec (hereinafter referred to as "ME30"), 3 min (hereinafter referred to as "ME3") and 24 hrs (hereinafter referred to as "ME24"), respectively, followed by washing with water.

(2) Example of stretching treatment

The biocatalyst-fixed membranes prepared as described above were subjected to a stretching treatment, which entailed attaching each membrane to a stretcher, placing the stretcher together with the attached membrane in a sealed box for 30 min in which the environment was held at a temperature of 20° C. and a relative humidity of 90%, thereafter stretching the membranes in the box at a tensioning rate of 0.2 mm/sec, and structurally stabilizing the membranes at given degree of stretching of 1.25X, 1.5X, 2.0X and 3.0X (hereinafter represented by DR1.25, DR1.5, DR2.0 and DR3.0) for 10 min and at a relatively humidity of 40% for 10 min.

Preservation of Biocatalyst-fixed Membranes

The biocatalyst-fixed membranes prepared as described above were preserved in a dry state at a temperature of 4° C. until biocatalyst stability was measured. Prior to measurement of biocatalyst stability, each biocatalyst-fixed membrane was dipped in a 0.1 M phosphate buffer solution (pH 7.0).

Biocatalyst Stability Measurement

The biocatalyst activities of the GOD-fixed *Bombyx mori* regenerated silk fibroin membranes were measured quantitatively by colorimetry and a dissolved oxygen electrode. The spectrophotometer used was a model U-3200 (manufactured by Hitachi, Ltd.), and the oxygen electrode was a model BO (manufactured by Ishikawa Seisakusho, K.K.). For comparison purposes, free GOD was also measured.

The amount of eluted protein was determined by the Lowry method.

The permeabilities of the membranes were measured by a differential birefringencemeter (manufactured by Nippon Bunseki Kogyo K.K.) using a 0.1 M aqueous glucose solution.

Structural Analysis and Measurement

A $^{13}C$ NMR measurement was carried out using an FX-90Q (manufactured by JEOL) at a frequency of 22.49 MHz and a temperature of 25° C.

An IR measurement (infra-red analysis) was performed using an IR-435 (manufactured by Shimazu Seisakusho K.K.).

Results of IR Measurement

The IR spectra of the stretched GOD-fixed regenerated silk fibroin membranes are illustrated in FIG. 1. Peak intensity at 700cm$^{-1}$ of the amide band V increased owing to the stretching treatment, and it was verified that silk fibroin membrane took partially $\beta$-form. Immediately after membrane formation (i.e. prior to stretching), there were many random coil regions in the silk fibroin membranes, and these would redissolve if the membranes were immersed in water as is. However, insoluble membranes could be fabricated by increasing the crystallization between the molecular chains of the silk fibroin, this being accomplished by mere stretching of the membranes. The $\beta$-form mentioned above refers to achieving hydrogen bonds between the molecular chains to provide a dense structure, thereby realizing structural stabilization to prevent elution of the fixed biocatalyst. The random coil regions refer to regions in which the biocatalyst readily dissolves in water because of comparatively little interaction between molecular chains.

Even when stretched Bombyx mori regenerated silk fibroin membranes not containing GOD were immersed in a phosphate buffer solution (pH 7.0), the amount of eluted protein Bombyx mori silk fibroin after 10 days was less than 0.02±0.01 w/w % in all cases.

Results of $^{13}C$ NMR Measurement

FIG. 2 illustrates $^{13}C$ NMR (nuclear magnetic resonance) spectra of the insolubilized GOD-fixed Bombyx mori regenerated silk fibroin membranes. Though considerable mobile components which give a high-resolution peak rem in in methanol-treated membranes B, these components are reduced in stretched membranes C. This indicates there is a highly non-homogeneous structure between the $\beta$-form regions near the surface and the internal mobile regions in the case of the methanol treatment, and that $\beta$-form tends to proceed through the entirety of the membrane when the stretching treatment is applied.

Results of Biocatalyst Stability Measurement by Colorimetry

Table 1 shows the results of determining, by colorimetry, the rate of hydrogen peroxide formation which accompanies the biocatalyst reaction of GOD-fixed Bombyx mori regenerated silk fibroin membranes.

TABLE 1

Rate of Hydrogen Peroxide Formation Accompanying biocatalyst Reaction of GOD-Fixed Bombyx mori Regenerated Silk Fibroin Membranes

| Stretching | Reaction Rate × 10$^4$ (Absorbance/min cm$^2$) | Reaction Rate × 10$^2$ (Absorbance/min mg) |
|---|---|---|
| DR 1.25 | 7.22 | 5.26 |
| DR 1.5 | 6.12 | 5.23 |
| DR 2.0 | 4.50 | 4.90 |
| DR 3.0 | 4.06 | 6.01 |
| Methanol Treatment | | |
| ME 30 (30 sec) | 6.5 | 3.87 |
| ME 3 (3 min) | 5.6 | 3.33 |
| ME 24 (24 hr) | 5.1 | 3.04 |

A comparison of the methanol-treated membranes and stretched membranes shows no great difference in reaction rate per unit surface area. However, in terms of reaction rate per unit weight of the biocatalyst, the comparison reveals that the stretched membranes tend to have higher reaction rates than the methanol-treated membranes in all cases.

As for the effect of degree of stretching on biocatalyst stability, reaction rate per unit surface area gradually declines with an increase in the percent of stretch. However, there is no significant change in reaction rate per unit amount of biocatalyst with a change in degree of stretch.

Results of Glucose Permeability Measurement

In many cases, the rate of reaction of fixed biocatalyst is influenced by the diffusion rate of the substrate in the carrier. Upon measuring the glucose permeability of the silk fibroin membrane, it was found that the permeability constant declined markedly with an increase in stretching, as shown in FIG. 3. This indicates that the biocatalyst reaction of a stretch-treated Bombyx mori regenerated silk filbrin membrane has a correlation with the permeability of glucose, which is the substrate.

Results of biocatalyst stability Measurement by Dissolved Oxygen Electrode

FIGS. 4(a), (b) are views illustrating the results of determining the biocatalyst activities of GOD-fixed Bombyx mori regenerated silk fibroin membranes by a dissolved oxygen electrode, and FIG. 5 is a table showing Michaelis constants Km and maximum reaction rates Vm obtained from FIGS. 4(a), (b), in which [S] represents the substrate concentration. These results show that the biocatalyst activities of the stretched GOD-fixed Bombyx mori regenerated silk fibroin membranes are higher overall than those of the methanol-treated membranes, and that the higher the stretching, the higher the biocatalyst stability.

The stability of biocatalyst stability with respect to a change in pH is shown in FIG. 6. It was found that the GOD-fixed Bombyx mori regenerated silk fibroin membranes have stability that is more stable than free GOD with respect to a change in pH, and that the pH range indicating relative actitivies of 80% or more is a broad pH 5-8.

Results of Measuring Glucose Sensor Characteristics

FIGS. 9(a), (b) are schematic views of a glucose sensor fabricated by coating an oxygen electrode with a GOD-fixed Bombyx mori regenerated silk fibroin membrane embodying the present invention. Numeral 91 denotes a well-known oxygen electrode, 92 a GOD-fixed *Bombyx mori* regenerated silk fibroin membrane, 93 a voltage measuring device, 94 a stirrer for stirring a glucose solution 96, and 95 a vessel through which thermostated water is passed to hold the glucose solution 96 at a constant temperature. FIG. 9(b) is an enlarged view of the tip of the glucose sensor. Numeral 91a denotes a platinum electrode, 91b an internal liquid chamber, and 97 a Teflon membrane having gas permeability. The Teflon membrane 97 is coated with the GOD-fixed *Bombyx mori* regenerated silk fibroin membrane 92. The characteristics of this glucose sensor were measured voltometrically by the voltage measuring device 93.

Figure 7:
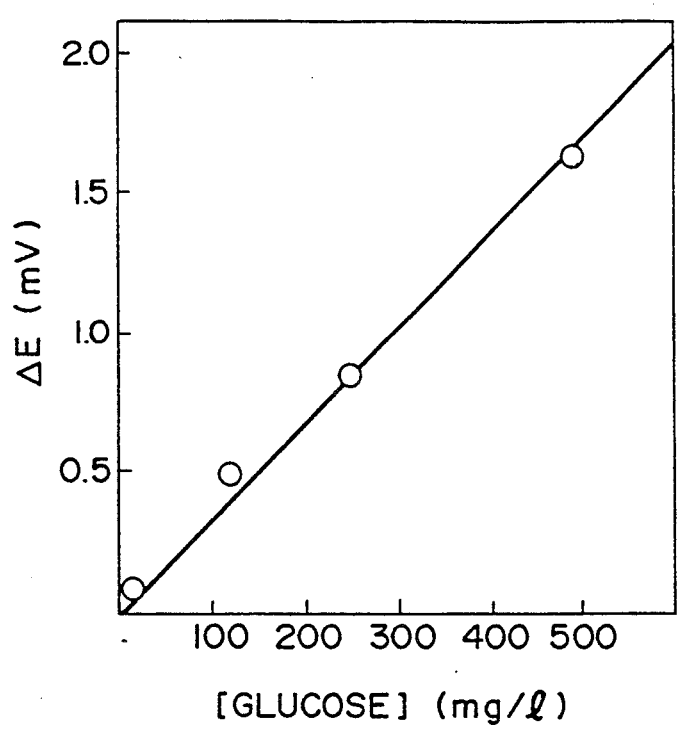
Figure 8:
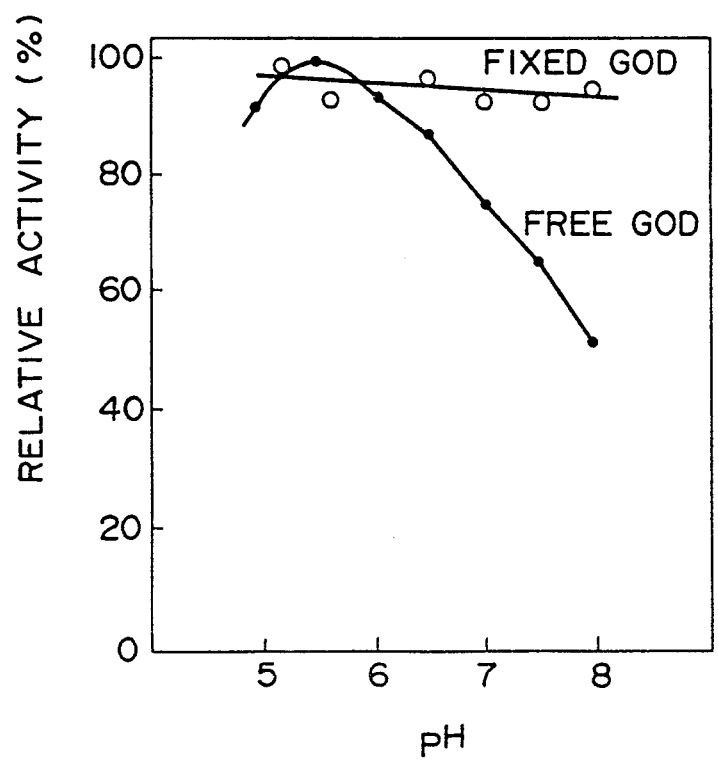
FIG. 8 is a graph illustrating the output stability of a glucose sensor with respect to a change in the pH of a glucose oxidase-fixed *Bombyx mori* regenerated silk fibroin membrane of Example 1.

FIGS. 7 and 10 are graphs in which the glucose sensor output voltage is plotted against glucose concentration, and FIG. 8 is a graph illustrating the stability of the glucose sensor output with respect to a change in pH. These graphs demonstrate that the GOD-fixed *Bombyx mori* regenerated silk fibroin membrane of the present embodiment can be used satisfactorily as the biocatalyst membrane of a glucose sensor, and that stability is high over a pH range of 5-8.

An ion sensor in accordance with the invention has excellent performance, as will now be illustrated.

Performance of a glucose sensor using a stretched *Bombyx mori* regenerated silk fibroin membrane as a biocatalyst-fixed carrier:
Shelf life: four months
pH dependence: stable (90% output) at pH 5- 8
biocatalyst elution: 0.01%/10 days
Response time: 8.5 sec (90% response)
Measurement range: 1- 500 mg/l
Repetitive measurement error: less 0.9% (30 runs)
  where GOD: aspergillus niger
  Fixation process: Entrapping method using stretching
  Membrane thickness: 23 um
  Effective Membrane surface area: 0.126 cm²

Thus, in accordance with the invention, there is provided an biocatalyst sensor using an biocatalyst-fixed membrane in which, by exploiting the structural characteristics of silk fibroin to employ the same as an biocatalyst *Bombyx mori* regenerated fixed material, the stability of the biocatalyst-containing membrane is raised, the leakage of biocatalyst is minimized and biocatalyst stability is prolonged.

In the biocatalyst sensor of the invention, the structural change of the biocatalyst-containing regenerated silk fibroin membrane is manifested solely by a stretching treatment without any chemical processing. As a result, the following advantages are obtained:

(1) The biocatalyst-containing membrane has a high stability yield.

(2) Stability is excellent when pH is changed.

(3) The stability of the biocatalyst in the membrane does not change for more than four months.

Though glucose is selected to typify the biocatalyst in the illustrated embodiment, it is obvious that other biocatalysts can be used. In addition, the technical concept of the invention is not limited to *Bombyx mori* but can also be applied to other biocatalyst-fixed membranes such as wild silkworm regenerated silk fibroin membranes, microbial membranes and membranes made of animal and vegetable cells.

EXAMPLE 2-1

Process for Preparing Silk Fibroin Solution

*Bombyx mori* cocoon was degummed with 0.5% marseilles soap at a cocoon-soap ratio of 1:200 for 30 min at a temperature of 100° C. After this was performed twice, the result was washed with distilled water to obtain degummed cocoon.

The degummed cocoon was dissolved at a temperature of 40° C. in a 9 M aqueous solution of lithium bromide (LiBr), and dialyzed after which approximately 4w/w % of a *Bombyx mori* regenerated silk fibroin solution was obtained.

Process for Preparing Biocatalyst-fixed Membrane

A glucose oxidase solution in an amount of 0.2 wt % of the weight of fibroin was mixed gently with the regenerated fibroin solution. The concentration of glucose oxidase is preferably 0.002% to 6%, and, if it is less than 0.002%, the response becomes deteriorated when glucose oxidase is applied to a biocatalyst sensor. If the concentration of glucose oxidase exceeds 6%, glucose is likely to elute from the biocatalyst-fixed membrane. The liquid was cast on an acrylic sheet and air-dried at 20° C., thereby providing a glucose oxidase-fixed silk fibroin membrane 1. A compression treatment was performed by placing the membrane in a shield box in an atmosphere at 20° C. and a relative humidity of 90%. The temperature is preferably −10° C. to 60° C. If the temperature is below −10° C., freezing is likely to occur, and, if it exceeds 60° C., the biocatalyst is likely to become deactivated. In addition, the relative humidity is preferably 70% or above, and, if it is less than 70%, the β-form region is not produced. The membrane was then removed and placed in a charta 2, and a predetermined pressure (at 560 kgf/cm² for two min. in this case) was applied thereto. Subsequently, the pressurized membrane was held for 10 min in an atmosphere at a humidity of 40% to achieve structural stabilization. The pressurizing force is preferably 140 to 700 kgf/cm², while the pressurizing time is preferably 1 min or more. If the pressurizing force is low and the time is short, both the biocatalyst and the silk fibroin elute from a preserving solution (phosphate buffer solution).

A methanol treatment for comparison was effected by immersing the membrane in a 80% aqueous solution for 30 sec followed by washing. The treated membrane was preserved in a 0.1 M phosphate buffer solution (pH 7.0) until the biocatalyst stability was measured.

EXAMPLE 2-2

A glucose oxidase solution in an amount of 0.002wt % of the weight of fibroin was fixed by a compression treatment in the same way as Example 2-1, therely preparing a GOD-fixed membrane.

EXAMPLE 2-3

*Pseudomonas fluorescens* which exhibits a GOD stability was fixed as microorganism with a fixing amount of 1.2 wt % by a compression treatment in the same way as the GOD-fixed membrane of Example 2-1, thereby preparing a microorganism-fixed membrane.

Evaluation of Stability

Glucose and oxygen undergo biocatalyst reaction due to glucose oxydase. By using a circuit similar to the one shown in FIG. 9(a) in the same way as in Example 1, measurement was made of the amount of oxygen consumed in this biocatalyst reaction by means of a commercially available biocatalyst electode 5 (a model BO manufactured by Ishikawa Seisakusho, K.K.) so as to evaluate the stability. Incidentally, measurement was similarly conducted with respect to free glucose oxidase- and methanol-treated fixed membranes to provide comparative examples.

Thermal Stability of Fixed Biocatalyst

Figure 12:
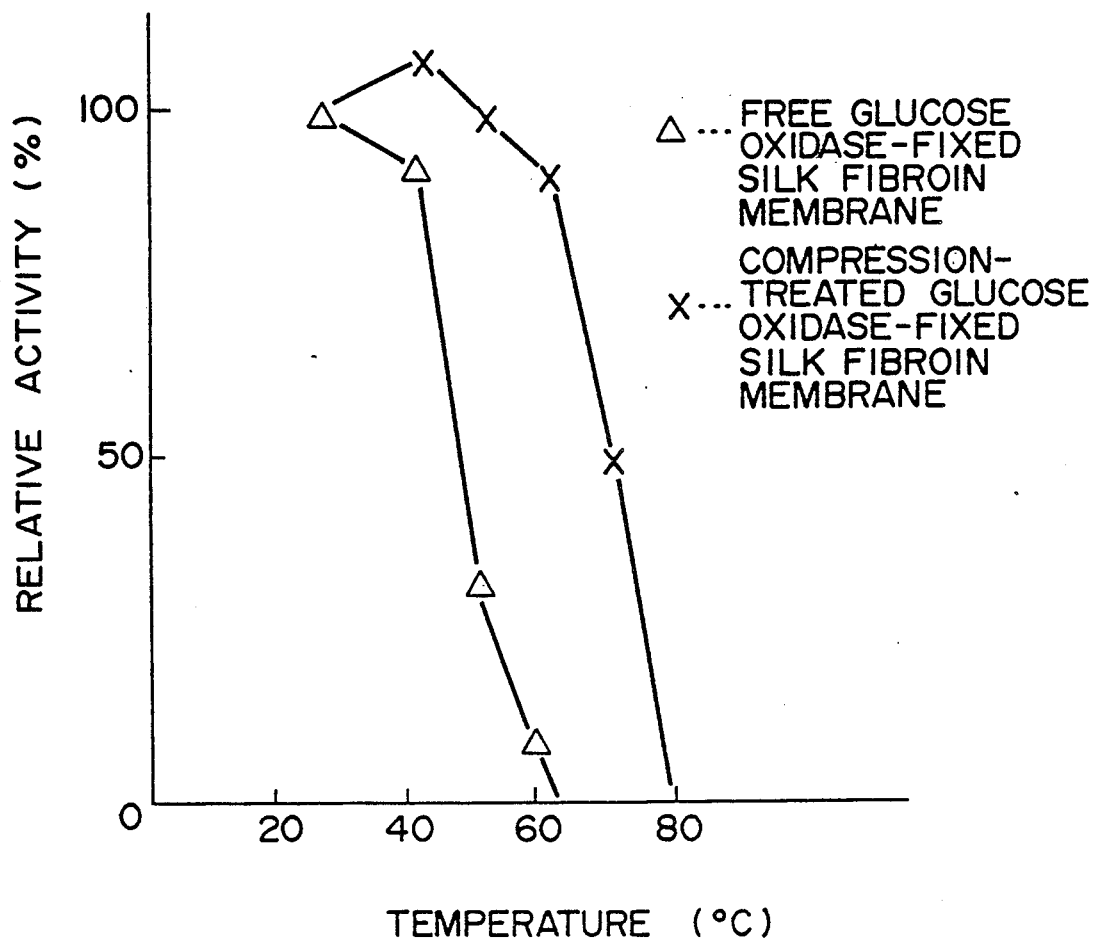
FIG. 12 is a graph showing the thermal stability of fixed-biocatalysts in glucose oxidase-fixed *Bombyx mori* regenerated silk fibroin membranes of Example 2.

Measurement was made of the relative stability with respect to membranes subjected to heat treatment at 30 min at a given temperature with room temperature (25° C.) set as 100. As a result, it was found that the compression-treated membranes displayed more excellent thermal stability than the free biocatalysts, as shown in FIG. 12.

Effect of the Presence of Ions

Measurement was made of the stability relative to the ion concentration by setting as 100 the stability at the time when ions were absent, so as to determine the effect of the presence of ions as impurities on the stability. As a result, it was found that the relative stability was stable, as shown in FIG. 13.

Strength and Degree of Stretching of membranes

The strength and degree of stretching were measured with respect to the compression-treated membranes in swollen as well as methanol-treated membranes and cellulose membranes of the prior art. The results are shown in Table 2, which reveals that the compression-treated membranes display greater values in both strength and degree of stretching than the other two types of membrane.

Incidentally, as for the cellulose membranes, those that are commercially available were used.

Although the numerical values of the strength and the standard deviation of the strength are measured values, those in the parentheses are comparative values in which the membrane thickness was uniformly set to the 10.3 um of the methanol-treated membrane.

Yield of Activity

Measurement was made of the activity yield of the compression-treated membranes and methanol-treated membranes of the prior art, and a comparison was made. The results are shown in Table 3. This table reveals that the activity yield is greater in the case of the compression-treated membranes.

TABLE 3

Activity Yield of Fixed biocatalysts Obtained by Methanol and Compression Treatments

| | Activity (U/mg) | Activity Yield (%) | Average Activity Yield |
|---|---|---|---|
| Free glucose oxidase | 107.00 | — | — |
| Methanol-treated | 5.38 | 5.00 | 4.77 |
| | 4.88 | 4.56 | |
| | 5.07 | 4.74 | |
| Compression-treated | 6.21 | 5.80 | 6.01 |
| | 6.21 | 5.80 | |
| | 6.88 | 6.43 | |

Response of Sensor

Figure 14A:
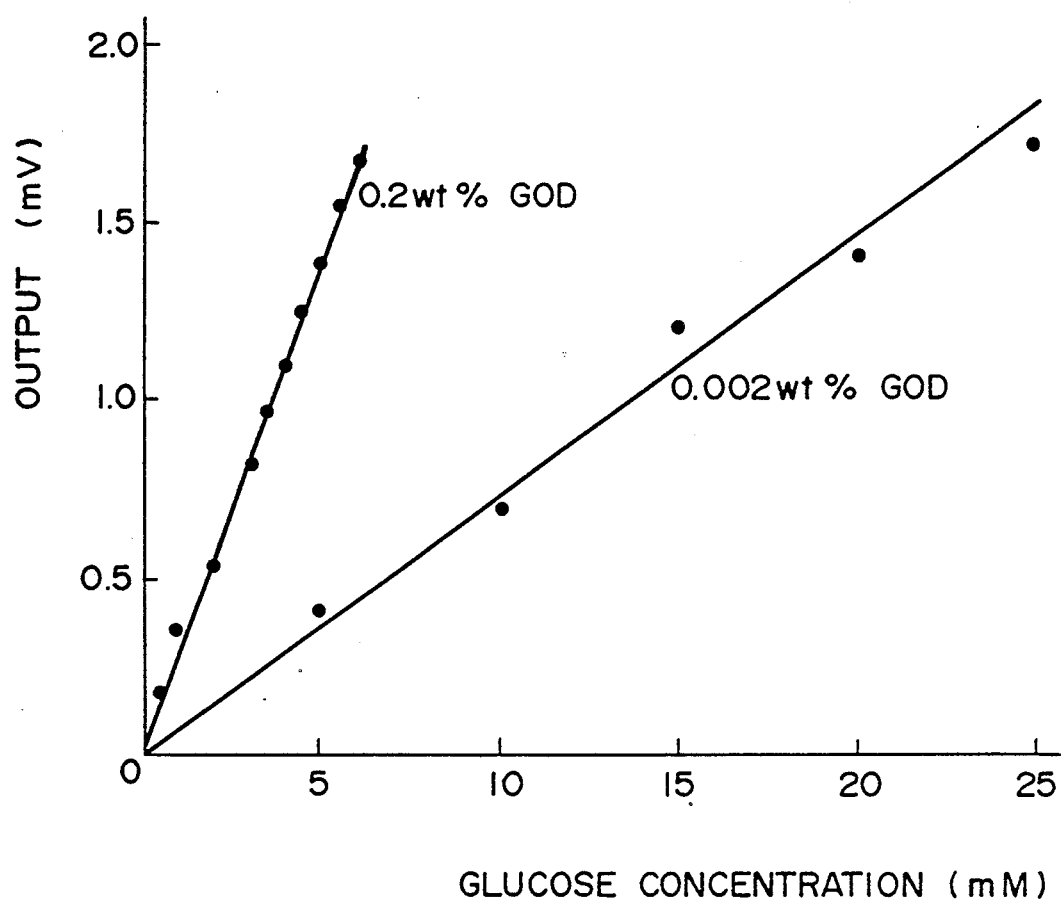
FIG. 14(a) is a graph in which the reduced output of the glucose sensor with the glucose oxidase-fixed *Bombyx mori* regenerated silk fibroin membranes is plotted against the amount of glucose added in the vessel.
Figure 14B:
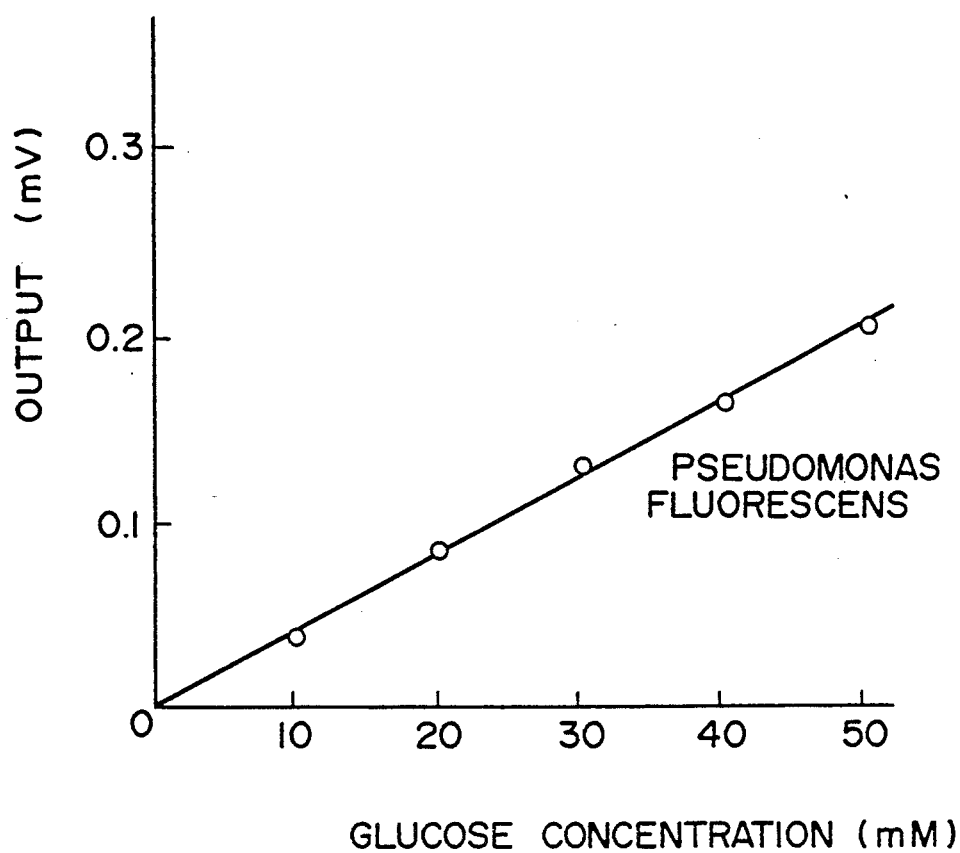
FIG. 14(b) is a graph in which the reduced output of the microorganism-fixed *Bombyx mori* regenerated silk fibroin membranes is plotted against the amount of glucose added in the vessel.

Above three membranes of Example 2 after a lapse of two months upon the compression treatment were respectively installed on a commercially available oxygen electrode (a model BO manufactured by Ishikawa Seisakujo K.K.) by means of an O-ring in the same way as in FIG. 9(a), and measurements were made of the response of the sensor when glucose was added gradually by predetermined amounts (0.27mg). The amount of glucose added was plotted as the absissas, and the amount of a reduced output was plotted as the ordinates. The results are shown in FIG. 14(a), (b), in which an extremely accurate calibration curve was obtained despite the fact that two months had elapsed after the compression treatment.

pH Stability of Sensor Response

Figure 14C:
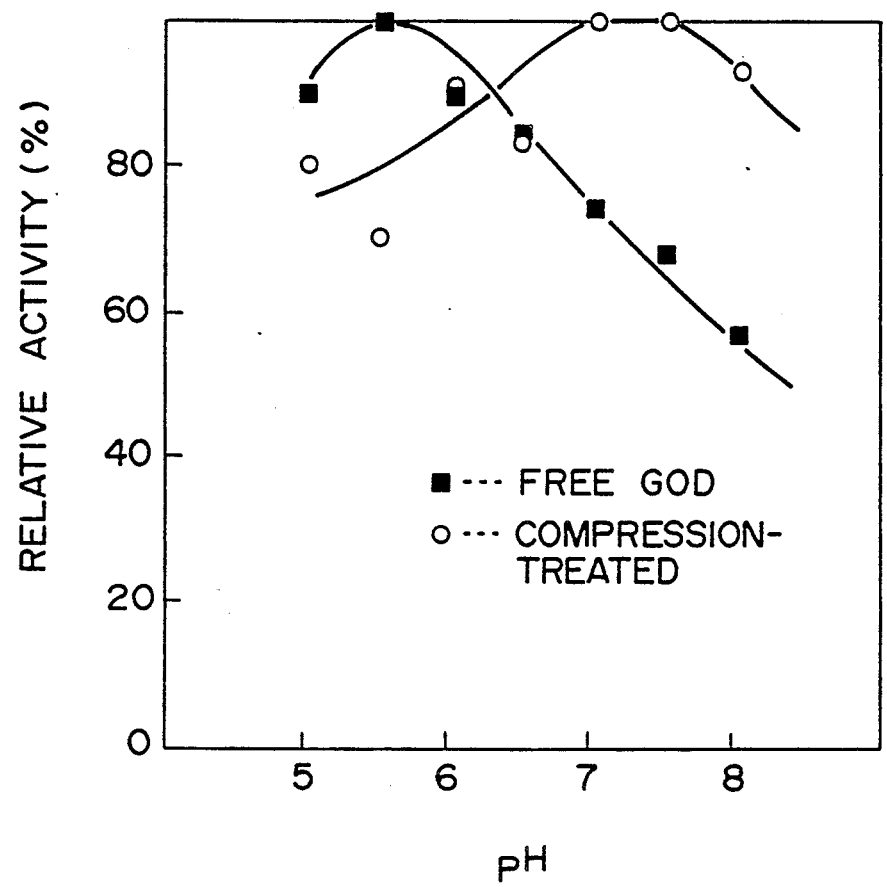
FIG. 14(c) is a graph in which the relation between the activities of free and fixed GOD *Bombyx mori* regenerated silk fibroin membrane of Example 2 is plotted against the change of pH.

After each membrane was dipped in an aqueous solution (0.1 M phosphate buffer solution) of various pH for two hours at 25° C., the stability was measured using a glucose solution of 7.0 pH. The results are shown in FIG. 14(c). The compression-treated membrane displayed a remarkably improved level of pH stability in the vicinity of neutrality as compared to the free GOD membrane.

Infra-red Analysis

An infra-red analysis (an IR measurement) was performed using an IR-435 (manufactured by Shimazu Seisakusho K.K.). The measured results are shown in FIG. 15. Peak intensity at 700cm$^{-1}$ of the amide V band increased owing to the compression treatment, and the occurrence of some $\beta$-regions was verified. The occurrence of $\beta$-regions mentioned above refers to achieving hydrogen bonds between the molecular chains to provide a dense structure, thereby making it difficult for the fixed biocatalyst to flow out. Immediately after membrane formation, there were many random coil

TABLE 2

Strength and Degree of Stretching of Methanol-, Compression-treated Fibroin Films and Cellulose Films in Swollen

| | Membrane (um) | Strength (kg/mm$^2$) | Standard deviation of strength | Degree of stretching (%) | Standard deviation of Stretching |
|---|---|---|---|---|---|
| Methanol-treated (30 min) | 10.3 | 6.07 | 1.12 | 189.1 | 49.9 |
| Compression-treated | 2.00 | 5.57 (28.7) | 1.29 (6.65) | 197.2 | 45.6 |
| Cellulose | 35.5 | 27.5 (8.10) | 1.30 (0.38) | 85.1 | 0 | regions in the domestic regenerated silk fibroin membranes, and these would redissolve if the membranes were immersed in water as is. However, insoluble membranes could be fabricated by increasing crystallization between the molecular chains of the silk fibroin, this being accomplished by mere compressing of the membranes.

It should be noted that the biocatalyst is not restricted to glucose oxidase alone, and it is apparent that the present invention can be applied to other biocatalysts as well.

It should be noted that the biocatalyst is not restricted to glucose oxidase or *Pseudomonas fluorescens*, and it is apparent that the present invention can be applied to other biocatalysts as well.

As many apparently widely different embodiments of the present invention can be made without departing from the spirit and scope thereof, it is to be understood that the invention is not limited to the specific embodiments thereof except as defined in the appended claims.

What is claimed is:

1. A method of manufacturing a silk fibroin membrane containing an entrapped biocatalyst comprising the steps of:
   (a) mixing a given amount of a biocatalyst solution with a silk fibroin solution to form a mixed solution;
   (b) forming a silk fibroin membrane containing the biocatalyst by casting the mixed solution on a substrate followed by drying; and
   (c) mechanicallly treating said silk fibroin membrane containing the biocatalyst in an atmosphere held at a given temperature and humidity to form the membrane into β-form and to structurally stabilize said membrane whereby said silk fibroin membrane containing an entrapped biocatalyst is formed.

2. The method according to claim 1, wherein said step (c) is a stretching treatment.

3. The method according to claim 1, wherein said biocatalyst is an enzyme.

4. The method according to claim 1, wherein said biocatalyst is a microorganism.

5. A silk fibroin membrane containing an entrapped biocatalyst prepared by the method of claim 1.

6. The silk fibroin membrane containing an entrapped biocatalyst according to claim 5, wherein said biocatalyst is an enzyme.

7. The silk fibroin membrane containing an entrapped biocatalyst according to claim 5, wherein said biocatalyst is a microorganism.

8. A method of manufacturing a silk fibroin membrane containing an entrapped biocatalyst comprising the steps of:
   (a) mixing a given amount of a biocatalyst solution with a silk fibroin solution to form a mixed solution;
   (b) forming a silk fibroin membrane containing the biocatalyst by casting the mixed solution on a substrate followed by drying; and
   (c) attaching said silk fibroin membrane containing the biocatalyst to stretching means;
   placing said stretching means for 30 min in an atmosphere held at a temperature of 20° C. and a relative humidity of 90%;
   stretching said silk fibroin membrane containing the biocatalyst at a stretching rate of 0.2 mm/sec to produce a stretched silk fibroin membrane containing the biocatalyst; and
   holding the stretched silk fibroin membrane containing the biocatalyst for 10 min and at a relative humidity of 40% for 10 min to structurally stabilize the membrane whereby said silk fibroin membrane containing an entrapped biocatalyst is formed.

9. A method of manufacturing a silk fibroin membrane containing an entrapped biocatalyst comprising the steps of:
   (a) mixing a given amount of a biocatalyst solution with a silk fibroin solution to form a mixed solution;
   (b) forming a silk fibroin membrane containing the biocatalyst by casting the mixed solution on a substrate followed by drying; and
   (c) placing said silk fibroin membrane containing the biocatalyst in an atmosphere at a temperature ranging from $-10°$ to $60°$ C. and a relative humidity of 70%; and
   compressing said silk fibroin membrane containing the biocatalyst in said atmosphere at a pressure of 140 to 700 $kgf/cm^2$ to structurally stabilize said silk fibroin membrane whereby said silk fibroin membrane containing an entrapped biocatalyst is formed.

10. A biocatalyst sensor comprising:
    an electrically conductive substrate;
    a gas-permeable layer coating said electrically conductive substrate and permeable to a given gas; and
    a silk fibroin membrane containing an entrapped biocatalyst coating said gas-permeable layer; said membrane being prepared by:
    (a) mixing a given amount of a biocatalyst solution with a silk fibroin solution to form a mixed solution;
    (b) forming a silk fibroin membrane containing the biocatalyst by casting he mixed solution on a substrate followed by drying; and
    (c) mechanically treating said silk fibroin membrane containing the biocatalyst in an atmosphere held at a given temperature and humidity to form the membrane into β-form and to structurally stabilize said membrane whereby said silk fibroin membrane containing an entrapped biocatalyst is formed.

11. The biocatalyst sensor according to claim 10, wherein said biocatalyst is an enzyme.

12. The biocatalyst sensor according to claim 10, wherein said biocatalyst is a microorganism.

* * * * *